(12) United States Patent
Bonutti

(10) Patent No.: US 6,630,000 B1
(45) Date of Patent: *Oct. 7, 2003

(54) METHOD OF USING BODY TISSUE

(75) Inventor: Peter M. Bonutti, Effingham, IL (US)

(73) Assignee: Bonutti 2003 Trust-A, Effingham, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/443,906

(22) Filed: Nov. 19, 1999

Related U.S. Application Data

(63) Continuation of application No. 09/263,006, filed on Mar. 5, 1999, now Pat. No. 6,132,472, and a division of application No. 08/834,028, filed on Apr. 11, 1997, now Pat. No. 5,888,219, and a division of application No. 08/590,193, filed on Jan. 23, 1996, now Pat. No. 5,662,710, and a division of application No. 08/273,028, filed on Jul. 8, 1994, now Pat. No. 5,545,222, and a division of application No. 07/728,247, filed on Aug. 12, 1991, now Pat. No. 5,329,486.

(51) Int. Cl.$^7$ .................................................. A61F 2/28
(52) U.S. Cl. ............................... 623/23.63; 623/23.51; 623/1.41; 623/1.42
(58) Field of Search ............................. 623/1.41, 1.42, 623/1.43, 915, 919, 23.51, 23.52, 23.57, 23.63, 23.72, 23.76, 16.11, 901; 600/36

(56) References Cited

U.S. PATENT DOCUMENTS

| 1,959,615 A | 5/1934 | Derrah |
| 2,433,815 A | 12/1947 | Laforge |
| 2,621,145 A | 12/1952 | Sano |
| 2,724,326 A | 11/1955 | Long |
| 2,955,530 A | 10/1960 | Nilo |
| 3,048,522 A | 8/1962 | Velley |
| 3,514,791 A | 6/1970 | Sparks |

(List continued on next page.)

FOREIGN PATENT DOCUMENTS

| CH | 117960 | 5/1927 |
| DE | 337437 | 5/1921 |
| FR | 1111677 | 3/1956 |
| JP | 6429266 | 1/1989 |

OTHER PUBLICATIONS

Brian A. Naughton, Hematopoiesis on Nylon Mesh Templates, vol. 18, Nos. 3 & 4, (1987), pp. 219–250.

Marcel E. Nimmi, Ectopic Bone Formation Is Enhanced in Senescent Animals Implanted with Embryonic Cells, Clinical Orthopaedic and Related Research 234, (1988), pp. 255–266.

John A. Bierly, Osseous Filtration: An Improved Technique for Bone Implantation, J. Periodontol, Jun. 1974, pp. 414–420.

*Primary Examiner*—Paul Prebilic
(74) *Attorney, Agent, or Firm*—Fleit, Kain, Gibbons, Gutman, Bongini & Bianco; Paul D. Bianco; Martin Fleit

(57) ABSTRACT

A method of using body tissue includes obtaining graft tissue. A medicinal substance is added to the graft tissue. The graft tissue is shaped to a predetermined configuration while the graft tissue is outside of a patient's body. The graft tissue is moved into the patient's body while the graft tissue has the predetermined configuration. While the graft tissue is in the patient's body, the graft tissue is allowed to expand and absorb liquid from the patient's body. A mechanical interlock may be established between the graft tissue and tissue in the patient's body during expansion of the graft tissue and absorption of liquid from the patient's body.

79 Claims, 7 Drawing Sheets

U.S. PATENT DOCUMENTS

| | | | |
|---|---|---|---|
| 3,894,530 A | * | 7/1975 | Dardik et al. ............ 623/23.72 |
| 4,298,002 A | | 11/1981 | Ronel et al. |
| 4,304,178 A | | 12/1981 | Haberle |
| 4,400,833 A | | 8/1983 | Kurland |
| 4,453,421 A | | 6/1984 | Umano |
| 4,501,269 A | | 2/1985 | Bagby |
| 4,502,159 A | * | 3/1985 | Woodroof et al. ....... 623/23.72 |
| 4,516,276 A | | 5/1985 | Mittelmeier et al. |
| 4,553,272 A | | 11/1985 | Mears |
| 4,554,686 A | | 11/1985 | Baker |
| 4,562,598 A | | 1/1986 | Kranz ......................... 623/18 |
| 4,642,120 A | | 2/1987 | Nevo et al. |
| 4,678,470 A | | 7/1987 | Nashef et al. |
| 4,718,916 A | | 1/1988 | Morscher .................... 623/23 |
| 4,743,229 A | | 5/1988 | Chu |
| 4,794,854 A | | 1/1989 | Swaim |
| 4,795,467 A | | 1/1989 | Piez et al. |
| 4,834,757 A | | 5/1989 | Brantigan |
| 4,846,835 A | | 7/1989 | Grande |
| 4,863,472 A | | 9/1989 | Tormala et al. |
| 4,888,022 A | | 12/1989 | Huebsch |
| 4,932,973 A | | 6/1990 | Gendler |
| 4,950,296 A | | 8/1990 | McIntyre |
| 4,961,740 A | | 10/1990 | Ray et al. |
| 4,963,489 A | | 10/1990 | Naughton et al. |
| 5,015,247 A | | 5/1991 | Michelson |
| 5,061,286 A | | 10/1991 | Lyle ............................ 623/16 |
| 5,062,843 A | | 11/1991 | Mahony, III |
| 5,073,373 A | | 12/1991 | O'Leary et al. |
| 5,082,670 A | | 1/1992 | Gage et al. |
| 5,084,050 A | | 1/1992 | Draenert |
| 5,101,720 A | | 4/1992 | Bianchi |
| 5,162,506 A | | 11/1992 | Hadden |
| 5,192,327 A | * | 3/1993 | Brantigan ................. 623/17.11 |
| 5,204,106 A | | 4/1993 | Schepers et al. |
| 5,329,846 A | | 7/1994 | Bonutti |
| 5,390,683 A | | 2/1995 | Pisharodi |
| 5,545,222 A | | 8/1996 | Bonutti |
| 5,662,710 A | | 9/1997 | Bonutti |
| 6,132,472 A | * | 10/2000 | Bonutti ................... 623/23.72 |
| 6,156,070 A | | 12/2000 | Incavo et al. ............ 623/23.52 |

* cited by examiner

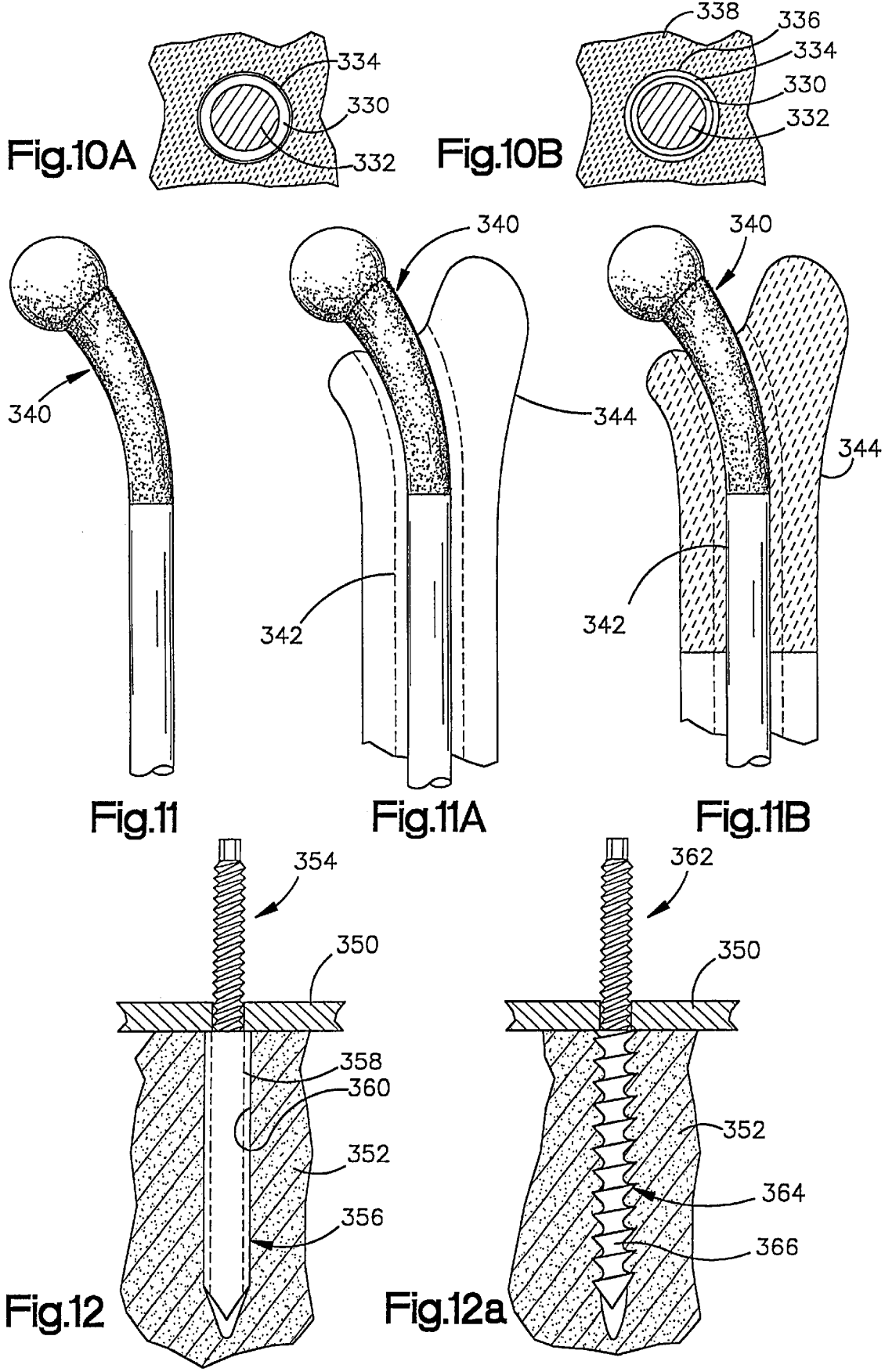

METHOD OF USING BODY TISSUE

This application is a continuation of application Ser. No. 09/263,006 filed Mar. 5, 1999, now U.S. Pat. No. 6,132,472. The aforementioned application Ser. No. 09/263,006 is itself a divisional of application Ser. No. 08/834,028 filed Apr. 11, 1997, now U.S. Pat. No. 5,888,219. The aforementioned application Ser. No. 08/834,028 is itself a divisional of application Ser. No. 08/590,193 filed Jan. 23, 1996, now U.S. Pat. No. 5,662,710. The aforementioned application Ser. No. 08/590,193 is itself a divisional of application Ser. No. 08/273,028 filed Jul. 8, 1994, now U.S. Pat. No. 5,545,222. The aforementioned application Ser. No. 08/273,028 is itself a divisional of application Ser. No. 07/728,247 filed Aug. 12, 1991, now U.S. Pat. No. 5,329,846. The benefit of the earlier filing dates of the aforementioned patents is claimed.

BACKGROUND OF THE INVENTION

Tissue grafting, including bone grafting, is well known. Tissue such as bone is removed from one part of a body (the donor site) and inserted into tissue in another (the host site) part of the same (or another) body. It is desirable to be able to remove a piece of tissue graft material which is the exact size and shape needed for the host site where it will be implanted. However, it is rarely possible to do this.

Accordingly, various tissue grafting techniques have been tried to solve this problem. For example, Nashef U.S. Pat. No. 4,678,470 discloses a method of creating bone graft material by machining a block of bone to a particular shape, or by pulverizing and milling it. The graft material is then tanned with glutaraldehyde to sterilize it. This process can produce bone plugs of a desired shape.

In the Nashef process, the exogenic bone material selected for the graft is presumably dead at the beginning of the process. The process of pulverizing or milling the bone material destroys the structure of the bone tissue. The step of tanning it with glutaraldehyde then renders the graft material completely sterile. This condition is not conducive to graft healing and ingrowth. Specifically, applicant has found that it is desirable to maintain graft tissue in a living state during the grafting process. The use of living tissue in a graft will promote bone healing.

SUMMARY OF THE INVENTION

The present invention is a tissue press for shaping or compressing a piece of tissue. The press includes first and second members movable relative to each other. First and second forming elements of different predetermined shapes are positionable on the first and second members on opposite sides of the piece of tissue. The first and second members are moved toward each other to shape or compress the tissue between the first and second forming elements.

Means are preferably provided for monitoring and controlling the amount of force or pressure applied to the piece of tissue, in order to maintain the tissue in a viable living condition. Means may also be provided for draining off fluid from compressed tissue, so that the tissue can be implanted in a compressed state and imbibe fluid from the host site.

The present invention is also a method of reshaping tissue for use as graft material comprising the steps of determining the shape which the tissue should possess as graft material; providing a tissue press, selecting forming elements adapted to press tissue approximately to the desired shape, and placing the forming elements on the tissue press; placing the tissue in the tissue press between the forming elements; operating the tissue press to shape the tissue between the forming elements to give the tissue the desired shape; and controlling the pressure on the tissue during the shaping step to minimize damage to or necrosis of the tissue.

The present invention is also a method which includes the steps of determining the shape and size which the tissue should possess as graft material; placing the tissue in a tissue press having forming elements adapted to press tissue approximately to the shape and size desired; compressing the tissue in the tissue press to give the tissue the shape and size desired; controlling the pressure on the tissue during the compressing step to minimize damage to or necrosis of the tissue; and draining off fluid expressed during the compressing step.

In accordance with another feature of the present invention, a retainer is provided for retaining tissue graft material in its compressed state. The retainer is placed around the compressed graft. The retainer can help to maintain the graft in a compressed configuration or in a specific shape for a period of time long enough to be placed in the body. The retainer may be made of a material which expands after it is placed in the body, to mechanically interlock the graft to the body.

General Description of the Invention

With the apparatus and method of the present invention, bone or other tissue can be compressed or reshaped or both, while preserving the tissue alive.

Reshaping

Often, reshaping of graft tissue is necessary to obtain the best possible graft. For example, in an anterior cruciate ligament reconstruction, the graft material which is removed usually has a triangular cross-sectional configuration. This graft material is placed in an opening in bone formed by drilling with a round drill. When the triangular graft material is placed in the round opening, there is minimal physical contact between the graft material and the surrounding bone. This reduces the holding power of the graft and also reduces the ingrowth ability of the graft.

Thus, an important feature of the present invention is that bone or other tissue such as ligament is reshaped while still leaving it in a whole condition and without substantial tissue damage. The tissue is placed in the tissue press of the present invention and sufficient force is applied to reshape the tissue to the desired shape—for example, a cylindrical shape as needed for an anterior cruciate ligament reconstruction. Excessive pressure on the tissue, which can damage or kill the tissue, is avoided as described below. A properly shaped graft is thus provided which is still in a living condition.

Compression

Compression of graft tissue is also sometimes desirable. Generally, tissue is stronger when it is more dense. Compressing graft tissue increases its density and thus strengthens the graft tissue. The graft tissue also stays together better.

For example, a tendon is made of a plurality of fibers. The individual fibers are weak when separated or unraveled. If a tendon graft is implanted with the fibers in a loose condition, the graft is weak. On the other hand, if prior to implantation the tendon graft is compressed to orient and pack the fibers tightly, then the entire group of fibers acts as one whole unit and the graft is much stronger. Therefore, compressing the tendon graft gives it more mechanical integrity—making a smaller tendon graft much stronger.

Similarly, bone tissue is stronger and better able to bear force when it is denser and more compact. Compressing bone graft tissue prior to implantation produces a stronger graft.

Compression of bone or other tissue also allows a surgeon to convert a larger irregular shape into a smaller specific shape. Thus, the surgeon when removing the graft material from the donor site is not limited by the conditions at the host site but can remove the graft material in the best way possible from the donor site. Similarly, the surgeon when implanting the graft material at the host site is not limited by the shape of the material removed (as dictated by the conditions at the donor site) but can implant the graft material in the best way possible to fit the conditions at the host site.

The anterior cruciate ligament, for example, attaches to the femur and tibia at specific isometric locations. When the ligament is being replaced in an anterior cruciate ligament reconstruction, typical uncompressed graft material can be many times the size of those locations. In such a case it is necessary to drill openings much larger than desired in the bone to attach the new ligament. The graft tendon then tends to fall eccentrically in this larger opening, the functional anatomy of the ligament can not be recreated, and the functioning of the knee joint is compromised.

However, if the graft material for the new ligament is compressed in accordance with the present invention, its size can be reduced substantially. This allows the surgeon to drill a substantially smaller opening in the bone to attach the new ligament/graft structure, so as to recreate the functional anatomy of the ligament.

With the present invention, it is also possible to make a composite graft. For example, the graft material for an anterior cruciate ligament reconstruction is preferably tendon in the middle with bone at both ends. In accordance with the apparatus and method of the present invention, bone tissue can be compressed around the ends of tendon tissue to form a substitute anterior cruciate ligament more closely approximating the original.

It should also be noted that tissues other than bone and tendon can be worked with the tissue press. For example, a surgeon can harvest liver cells or pancreas cells and then compress them into a particular shape. They can then optionally be placed into a sack or some type of structural support which can be introduced into the body.

With the present invention, graft material can be formed into almost any shape. A specific pair of forming (mold) parts, having a desired predetermined shape, are positioned on the tissue press, and the tissue is shaped or compressed between the forming elements. In addition to three-dimensional shaped parts, it is also possible to make a flat piece of graft material. For example, shaved skin can be placed on a flat plate, perhaps on a retaining mesh. The cells are then subjected to pressure to adhere them together. A flat, even, piece of graft material is formed which is suitable for skin grafting.

Compressing graft material in accordance with the present invention also allows the surgeon to build up a larger piece of graft material out of several smaller parts. Sometimes a relatively large piece of graft material is needed for a particular host site. It is often not feasible to take such a large piece of graft material without damaging the donor area. To avoid this problem, several smaller pieces of graft material are placed in the tissue press and pressure is used to at least temporarily form the smaller parts together as one larger whole. The larger graft piece is then inserted into the host site.

Compressing graft material in accordance with the present invention also aids in introducing additional materials to the graft material. These additional materials could be antibiotics, bone growth enhancers, tri-calcium phosphate, fibrin, allograft or autograft material, etc. When added to the graft material under pressure, the added materials adhere to and become a part of the graft material and not merely something added to the surface of it. By combining physiologic solutions or a carrier such as a gelatin, polysaccharides, antibiotics or synthetic bone materials to the compressed bone, for example, it is possible to create a plug of living bone with the other materials added to it. This plug has the graft properties of the bone tissue in the plug, as well as the properties of the added material. Many of the additional materials, for example, the antibiotics and physiologic solutions, are medicinal substances.

When tissue is compressed, fluid may be forced out of (expressed from) the tissue. If tissue in this compressed and defluidized state it laid back in a tissue pouch or in a bone hole, body fluids from the host site are absorbed by the graft material. This imbibition causes swelling of the graft material and thus creates a mechanical interlock between the graft and the host. Such a mechanical interlock is not produced with a typical implantation process in which graft tissue is not compressed. Further, the swelling (enlarging) of the graft material allows the graft material to fill an opening of any given shape with a perfect fit of the graft material therein.

Pressure monitoring and controlling

As noted above, applicant has found that it is desirable to maintain bone graft tissue in a living state during the grafting process. It is important not to kill tissue used in grafting because the living graft cells provide a superior substrate for grafting and graft viability and improved tissue healing. There is significantly faster incorporation of living tissue than of dead tissue. The cells and the tissue that are implanted into the body therefore need to be maintained in a viable condition.

Excess pressure on tissue can cause destruction of the tissue, disorganization of the tissue fibers and irregular mechanical structure which can damage the tissue graft. Thus, a feature of the present invention is that the pressure or force on the tissue being reshaped or compressed is monitored and controlled. Pressure can be monitored by suitable pressure sensors and readouts such as a pressure gauge. Pressure can be controlled by force limiting means such as a torque wrench or similar device.

The desired pressure levels may vary. For example, it may be desirable to provide a higher compressive force for cortical bone than for cancellous bone. Similarly, it may be desirable to provide a higher compressive force for bone than for tendon tissue. The appropriate level of pressure or force is selectively available with the tissue press.

Retainers

A separate device or structure can be used to maintain graft tissue in the compressed state prior to and during implantation. This separate device or structure can be a mesh sack, a ring around a cylindrically shaped graft material, etc. This additional retainer structure can assist the surgeon in introducing the graft tissue into the body in the compacted condition, to provide a denser stronger graft and to allow imbibition for creating a mechanical interlock. The retainer can be made of a material which expands when placed in the body, to provide a mechanical interlock for the graft tissue.

BRIEF DESCRIPTION OF THE DRAWINGS

The foregoing and other features of the present invention will become apparent to one skilled in the art upon a consideration of the following description of the invention with reference to the accompanying drawings, wherein:

FIGS. 10A and 10B illustrate an expanding tissue retainer;

FIGS. 11, 11A and 11B illustrate an expanding surgical implant; and

FIGS. 12 and 12A illustrate expanding surgical stabilization devices.

DESCRIPTION OF PREFERRED EMBODIMENTS OF THE INVENTION

Figure 1:
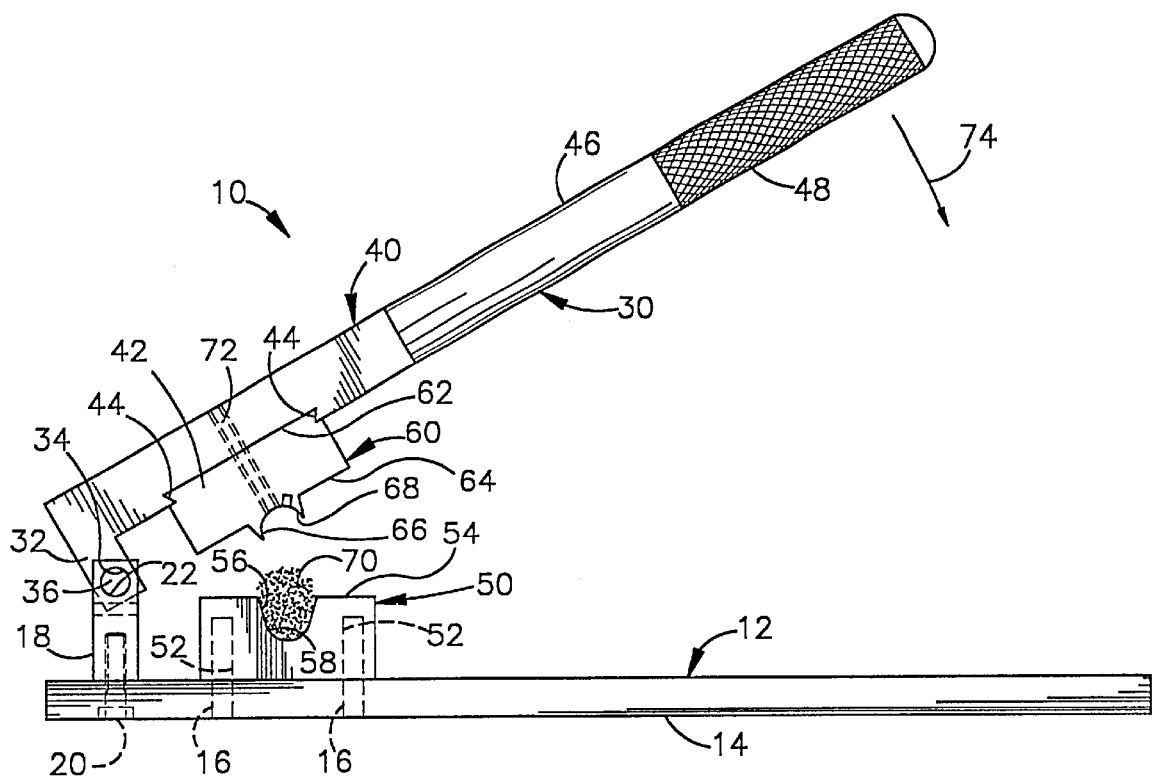
FIG. 1 is an elevational view of a tissue press embodying the present invention.

The present invention relates to a tissue press and particularly to a tissue press for shaping or compressing bone or other tissue. The present invention is applicable to various constructions of tissue shaping or compressing apparatus. As representative of the present invention, FIG. 1 illustrates a tissue press 10.

The tissue press 10 includes a base 12. The base 12 has a support surface 14 for supporting the base 10 and thus the press 10 on a table or other support (not shown). The base 12 has the same longitudinal cross-section throughout its width as is seen in elevation in FIG. 1. Two cylindrical pins 16 protect upwardly from the base 12. A U-shaped saddle 18 is secured to the base 12 by screws 20. A pin opening 22 extends transversely through the saddle 18.

The tissue press 10 also includes a handle 30. The handle 30 has a connector portion 32 received between the upwardly projecting side portions of the saddle 18 of the base 12. A pin opening 34 extends transversely through the connector portion 32 of the handle 30. The opening 34 is aligned with the opening 22 in the saddle 18. A pivot pin 36 extends through the pin openings 34 and 22 in the handle 30 and base 12, respectively, and pivotally connects the handle 30 to the base 12.

Extending from the connector portion 32 of the handle 30 is a form-supporting portion 40 of the handle 30. A channel 42 is defined on the lower side of the form supporting portion 40 between a pair of channel surfaces 44. The channel 42 extends transversely across the width of the form-supporting portion 40. Extending from the form-supporting portion 40 is a circular portion 46 of the handle 30. The circular portion 46 has a manually engageable surface 48 for the application of force to the handle 30.

A first forming element 50 is slidably received on the base 12. The first forming element 50 has two vertically extending pin openings 52 which receive the pins 16 of the base 12. The first forming element 50 has an upper surface 54 which includes a forming surface 56. The forming surface 56 has a cylindrical surface portion 58. The first forming element 50 has the same longitudinal cross-section throughout its width as is seen in elevation in FIG. 1. It should be understood that the first forming element 50 can be connected with the base 12 in any other suitable manner.

A second forming element 60 is slidably received in the channel 42 of the handle 30. The second forming element 60 has two projecting edges 62 which engage the channel surfaces 44 of the handle 30. The second forming element 60 has a lower surface 64 which includes a forming surface 66. The forming surface 66 includes a cylindrical surface portion 68. The second forming element 60 has the same longitudinal cross-section throughout its width as is seen in elevation in FIG. 1. It should be understood that the second forming element 60 can be connected with the handle 30 in any other suitable manner.

In operation of the press 10, a pair of forming elements 50 and 60 are selected which when brought together will shape a piece of living tissue 70 to the desired shape. For example, the forming elements 50 and 60 illustrated in FIG. 1 have cylindrical surface portions which will shape tissue into a cylindrical shape suitable for insertion into a round drill hole in bone. The first forming element 50 is slid onto the pins 16 on the base 12. The second forming element 60 is slid into the channel 42 in the handle 30. A set screw 72 is tightened to secure the second forming element 60 to the handle 30.

The piece of tissue 70 to be shaped is placed between the first and second forming elements 50 and 60. The tissue 70 is preferably positioned on the forming surface 56 of the first forming element 50 as illustrated in FIG. 1. The handle 30 is then brought toward the base 12 in the direction indicated by the arrow 74, by the application of force to the handle 30. The forming surface 66 with its cylindrical surface portion 68 engages the tissue 70, and forces the tissue 70 against the forming surface 56 with its cylindrical surface portion 58. The tissue 70 is thereby formed to the desired shape.

It should be understood that with the tissue press 10, tissue can be reshaped only, or reshaped and compressed. The amount and type of work performed on the tissue depends on the particular application, and is controlled by (i) the particular forming elements selected by the operator of the tissue press, and (ii) the amount of pressure or force applied to the tissue. For example, the forming elements can be selected so that they define between them a forming chamber having the same initial volume as the piece of tissue to be shaped. In this case, the piece of tissue is not compressed (that is, reduced in volume), but is merely reshaped. Alternatively, forming elements can be selected which will not merely reshape the piece of tissue but also will compress it, as described above. Because the first and second forming elements 50 and 60 are removably received on the base 12 and handle 30, respectively, the surgeon can easily select first and second forming elements 50 and 60 to reshape or compress the tissue 70 as desired.

As discussed above, it is important to control the pressure on the tissue in the tissue press 10. There are many ways to do this. For example, in the press 80 shown in FIGS. 2 and 3, a second forming element 84 has an opening 82 which extends between its upper surface 86 and its forming surface 88. An opening 90 in the handle 92 is aligned with and in fluid communication with the opening 82. A pressure monitor device indicated schematically at 94 is in fluid communication with the opening 90 in the handle 92, and thus with the forming surface 88 on the second forming element 84. The pressure monitor device 94 can be any known device for displaying pressure, such as a dial readout, a bar movable axially in the openings 82 and 90 in response to fluid pressure, etc. The pressure monitor device 94 displays the pressure at the forming surface 88 of the second forming element 84. This is the pressure applied to the tissue being pressed in the press 80. Thus, an operator of the press 80 can observe this pressure monitor device 94 and limit the applied force accordingly, in order to avoid tissue damage or necrosis.

Alternatively, a strain gauge of a known construction, indicated schematically at 96, can be placed on the forming surface 88 of the second forming element 84. Electric wires (not shown) transmit signals from the strain gauge 96 to an electric readout device indicated schematically at 94. The electric readout indicates electrically the pressure applied to the tissue in the press 80. Again, one can observe this pressure monitor device and limit the amount of force applied, in order to avoid tissue damage or necrosis. It should be understood that similar ways of monitoring the pressure on the tissue being pressed are the equivalent and are thus included within the scope of the invention.

Any of the tissue presses of the present invention can include means for cutting off excess tissue. As an example, FIGS. 3A and 3B illustrate a tissue press 91 having an independent cutoff arm 93 pivotally mounted adjacent the handle 95. The cutoff arm 93 has a blade portion 97 operable to cut off excess tissue compressed by the tissue press 91. The cutoff arm 93 is, of course, merely illustrative of the many equivalent structures usable to remove excess tissue after the compressing or shaping operation. Thus, the length of the tissue graft material, as well as its compressed diameter, can be selectively controlled by operation of the tissue press. It should be noted that this cutting off process can be effected with the edges of the forming elements themselves, as illustrated in the apparatus in FIG. 5.

As noted above, the first forming element 50 and the second forming element 60 are removably received on the base 12 and handle 30, respectively. Thus, forming elements having forming surfaces with other shapes can be easily placed in the tissue press 10, in order to shape or compress tissue into other shapes. A few of the many shapes obtainable are illustrated in FIG. 4.

Figure 2:
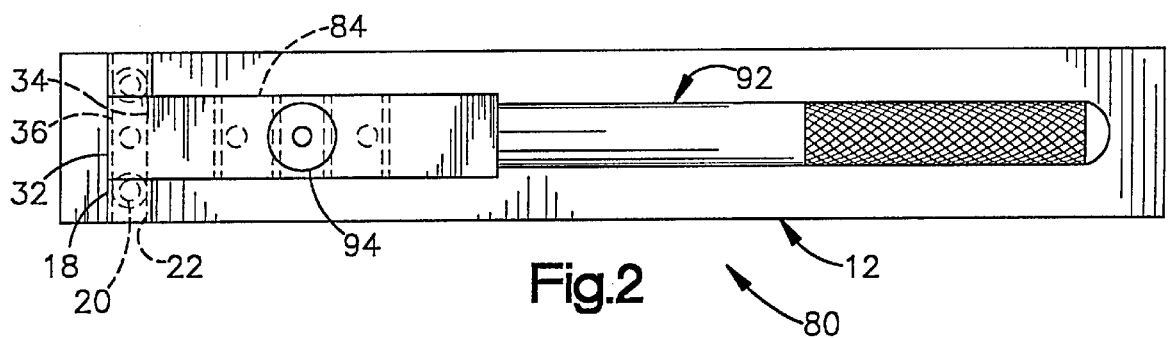
FIG. 2 is a top plan view of a tissue press similar to the tissue press of FIG. 1 and having a pressure sensing and monitoring mechanism.
Figure 3:
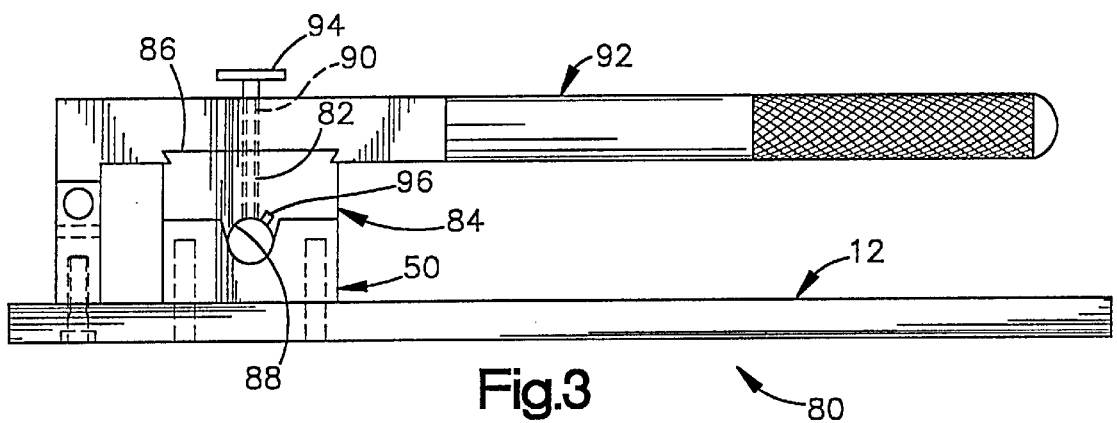
FIG. 3 is an elevational view of the tissue press of FIG. 2.
Figure 3A:
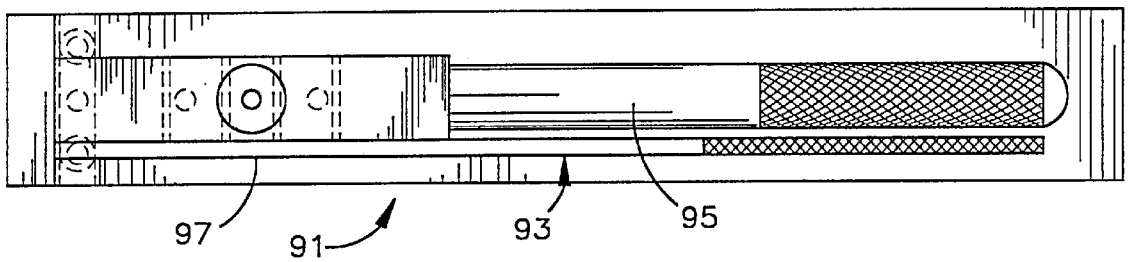
FIGS. 3A and 3B illustrate a tissue press having means for removing excess tissue after compression.
Figure 3B:
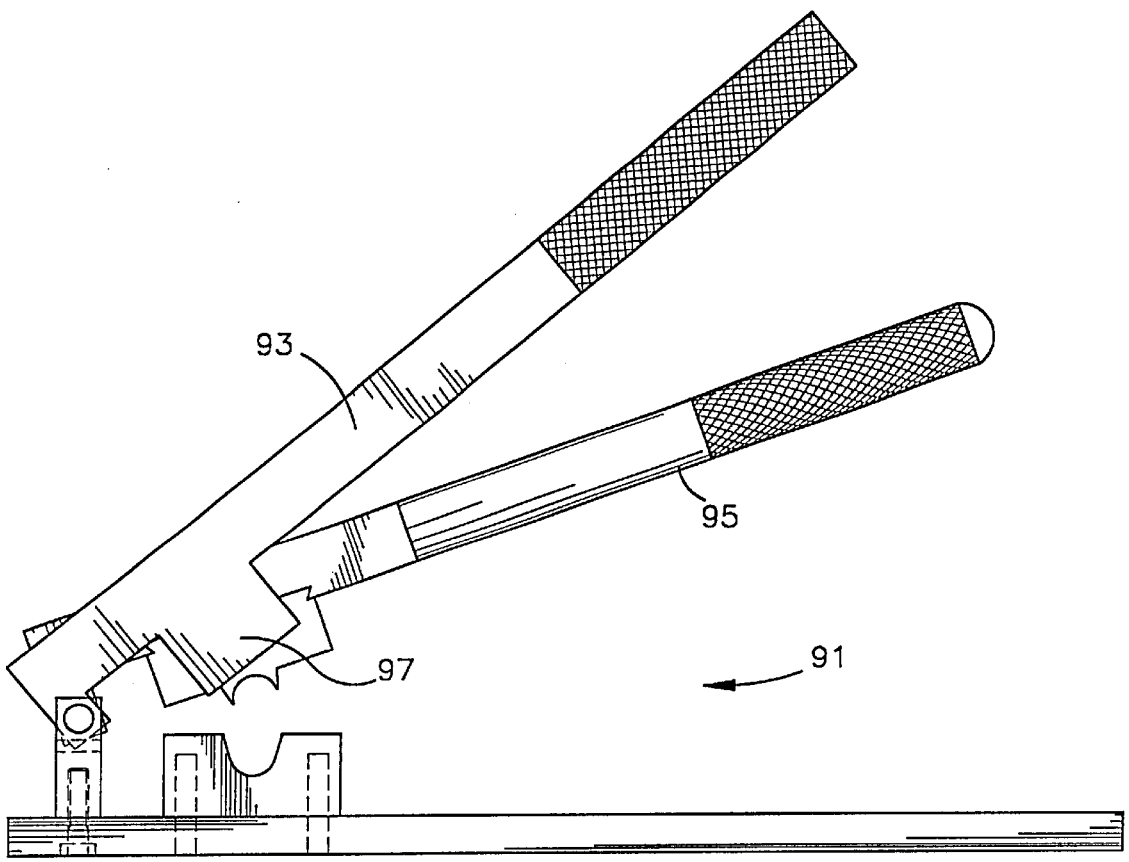
Figures 4A, 4B, 4C, 4D, 4E, 4F:
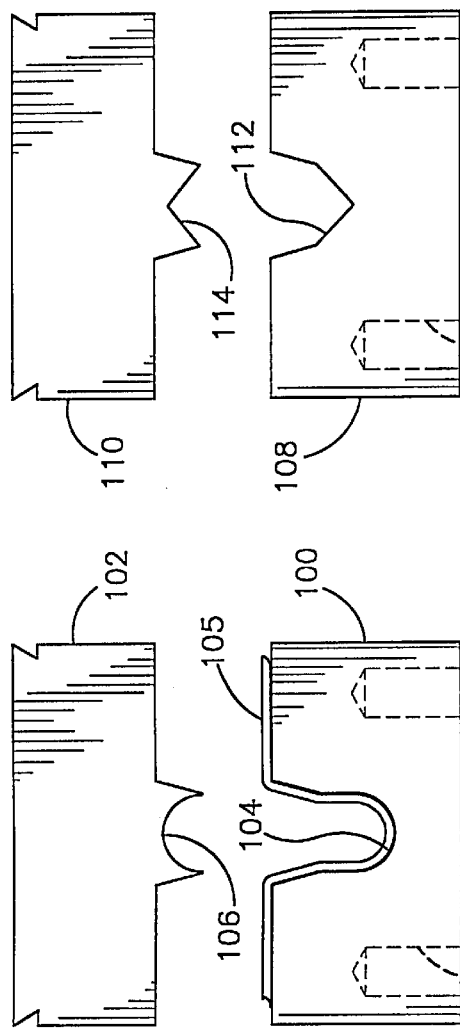
FIGS. 4A–4F illustrate a plurality of different forming elements for use in the tissue press of FIGS. 1–3.

FIG. 4A, for example, illustrates the forming elements 50 and 60 of FIGS. 1–3 which shape tissue into a cylindrical cross-sectional shape. FIG. 4B illustrates forming elements 100 and 102 which shape tissue into an oblong cross-sectional shape, between a forming surface 104 on the first forming element 100 and a forming surface 106 on the second forming element 102. FIG. 4C illustrates forming elements 108 and 110 which shape tissue into a square cross-sectional shape, between a forming surface 112 on the first forming element 108 and a forming surface 114 on the second forming element 110.

FIG. 4D illustrates forming elements 116 and 118 which shape tissue into a triangular cross-sectional shape, between a forming surface 120 on the first forming element 116 and a forming surface 122 on the second forming element 118. FIG. 4E illustrates forming elements 124 and 126 which shape tissue into a generally flat shape, between a forming surface 128 on the first forming element 124 and a forming surface 130 on the second forming element 126. FIG. 4F illustrates forming elements 132 and 134 which shape tissue into a semi-circular cross-sectional shape, between a forming surface 136 on the first forming element 132 and a forming surface 136 on the second forming element 134. Again, it should be understood that other shapes are conceivable and consequently are included within the scope of the invention.

In addition to three-dimensional shaped parts, it is also possible to make a flat piece of graft material. Forming elements like those shown in FIG. 4E are useful in this case. For example, a skin graft may be placed on an adhesive based mesh (possibly using fibrin) on the flat forming surface 128. The cells are then subjected to pressure to adhere them together. The cells are spread out over a finer layer. A flat, even, piece of skin graft material is formed. This can then be cut or pressed or formed into a specific shape and then used as a skin substitute on the body.

Any forming element useful in the present invention can be coated with a non-stick coating to reduce adhesion of the compressed tissue to the forming elements. For example, the forming element 100 (FIG. 4B) is indicated as having a non-stick coating 105 such as a Teflon® coating which may be applied in any suitable known manner. Such a coating can resist the binding of the tissue (or tissue additive such as fibrin discussed below) to the forming element.

Figure 5:
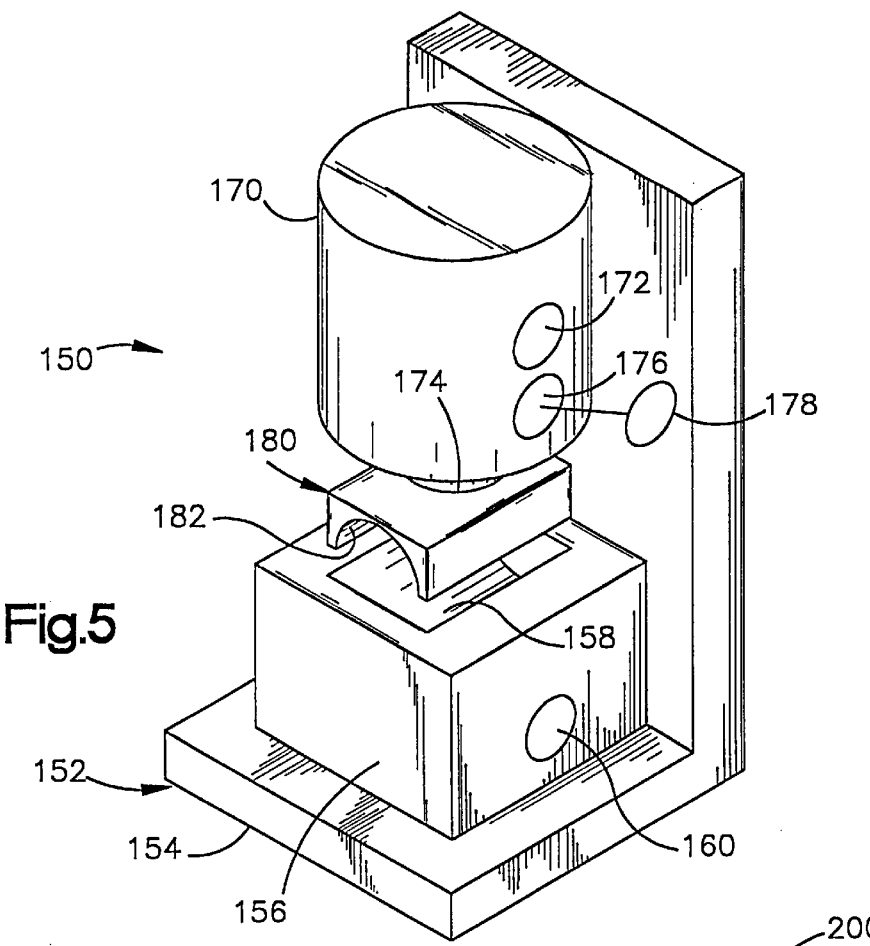
FIG. 5 is a view of a tissue press in accordance with a second embodiment of the invention.

In a second embodiment of the invention, illustrated in FIG. 5, a tissue press 150 is fluid operated (pneumatic or hydraulic) rather than manually operated. The press 150 includes a base 152 having a support surface 154 for supporting the base 152 and thus the press 150 on a table or other support (not shown). A first forming element 156 is attached to the base 152. The first forming element 156 may be slidably or otherwise attached to the base 152 in any suitable manner which blocks movement of the forming element 156 relative to the base 152 during operation of the press 150 and which allows for easy interchange of forming elements 156. The first forming element 156 has an upwardly facing forming surface 158. A fluid drain opening 160 is in fluid communication with the forming surface 158 of the first forming element 156.

An air or hydraulic cylinder 170 is fixed to the base 152 above the first forming element 156. The cylinder 170 has a port 172 for the introduction of air or other fluid under pressure to operate a piston 174 in a known manner.

A second forming element 180 is connected to the piston 174. The second forming element 180 is attached to the piston 174 in any suitable manner which blocks movement of the forming element 180 relative to the piston 174 during operation of the press 150 and which allows for easy interchange of forming elements 180. The second forming element 180 has a forming surface 182 facing the forming surface 158 on the first forming element 156.

A port 176 in the cylinder 170 is in fluid communication with the forming surface 182 of the second forming element 180. Connected to the port 176 is a pressure monitor device shown schematically at 178.

In operation of the press 150, a pair of forming elements 156 and 180 are selected which when brought together will shape tissue to the desired shape. The first forming element 156 is attached to the base 152. The second forming element 180 is attached to the piston 174. A piece of tissue to be shaped (not shown) is placed between the first and second forming elements 156 and 180. The piece of tissue is preferably positioned on the forming surface 158 of the first forming element 156.

The cylinder 170 is then actuated to move the second forming element 180 toward the first forming element 156. The forming surface 182 on the second forming element 180 engages the tissue, and forces the tissue against the forming surface 158 on the first forming element 156. Pressure on the tissue is controlled through observation of the monitor device 178. The tissue is formed to the desired shape. Again, it should be understood that with the press 150 tissue can be reshaped only, or compressed also, depending on the application, the forming elements selected, and the amount of force applied.

As discussed above, when tissue is compressed, fluid may be expressed from the tissue. In the press 150, the second forming element 180 fits within the first forming element 156 to define between them a closed forming chamber in which the tissue is compressed. Expressed fluid is drained from the forming chamber through the fluid drain opening 160. If a closed forming chamber is not formed, as for example with the open-ended forming elements shown in FIGS. 1–4, then expressed fluid can drain outwardly from the tissue being pressed, without the need for a separate fluid drain port. Of course, a separate fluid drain port could be provided in any of the forming elements of the present invention.

Figure 6:
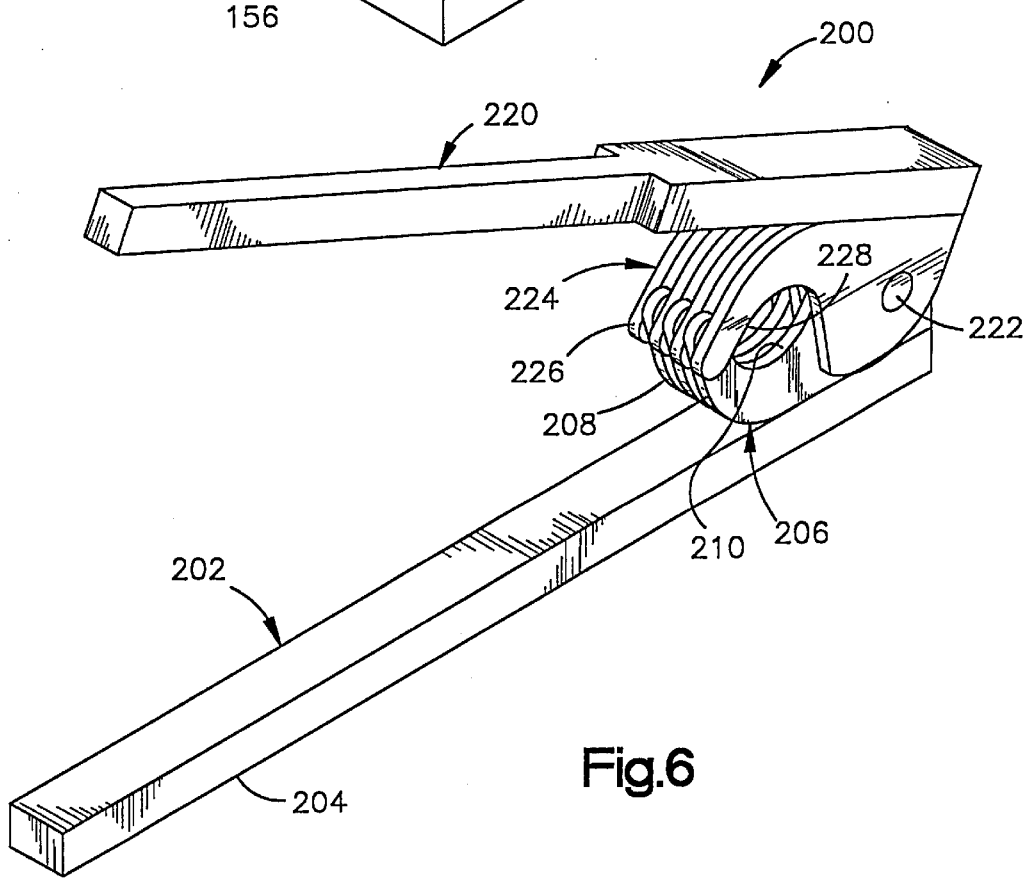
FIG. 6 is a view of a tissue press in accordance with third embodiment of the invention.

In a third embodiment of the invention, illustrated in FIG. 6, a tissue press 200 includes a base 202 having a support surface 204 for supporting the base 202 and thus the press 200 on a table or other support (not shown). A first forming element 206 is attached to the base 202. The first forming element 206 may be slidably or otherwise attached to the base 202 in any suitable manner. The first forming element 206 includes a plurality of first fingers 208 which together have a forming surface 210 to progressively compress bone or other tissue into a predetermined shape.

An upper arm 220 is pivotally mounted to the base 202 by a pivot pin 222. A second forming element 224 is connected to the upper arm 220 in a suitable manner. The second forming element 224 includes a plurality of second fingers 226 which together have a forming surface 228 facing the forming surface 210 on the first forming element 206. The second fingers 226 are interdigitable with the first fingers 208.

In operation of the press 200, a pair of forming elements 206 and 224 are selected which when brought together will progressively shape tissue to the desired shape. The first forming element 206 is attached to the base 202. The second forming element 224 is attached to the upper arm 220. A piece of tissue to be shaped (not shown) is placed between the first and second forming elements 206 and 224. The piece of tissue is preferably positioned on the forming surface 210 of the first forming element 206. The upper arm is pivoted toward the base to move the second forming element 224 toward the first forming element 206. The forming surface 228 on the second forming element 224 engages the tissue, and forces the tissue against the forming surface 210 on the first forming element 206. The tissue is formed to the desired shape.

Because the second fingers 226 are interdigitable with the first fingers 208, the press 200 is operable to compress tissue to different compressed sizes with only one pair of forming elements. As the second fingers 226 come together with the first fingers 208, they compress the tissue to a smaller and smaller diameter (shape). This allows for one pair of forming elements to provide compression to variable diameters or sizes. This works well with soft tissue applications, specifically tendons, to compress the tendon into a smaller shape. The amount of compression is based on the amount of pressure applied and the needed finished size.

Figure 6A:
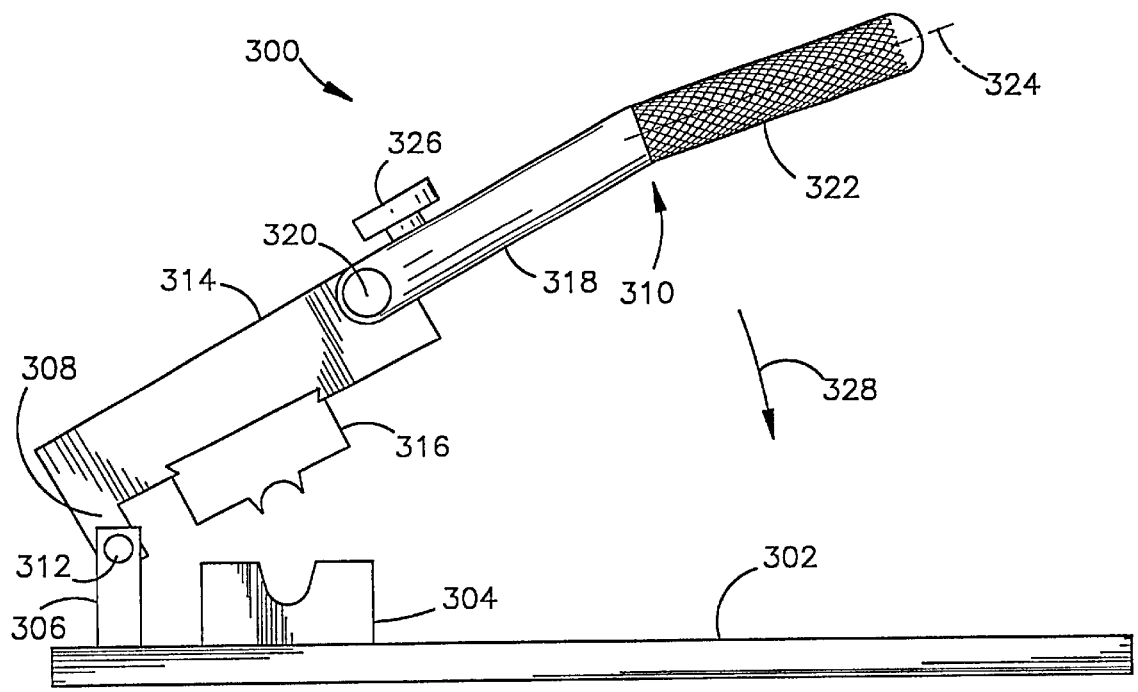
FIG. 6A illustrates a tissue press having means for limiting the amount of pressure applied to the tissue.

As noted above, it is important to control the pressure or force applied to the tissue by the tissue press. Accordingly, the present invention provides means for limiting the amount of pressure applied to the tissue by the tissue press, that is, means for blocking application to the tissue of force in excess of a predetermined amount. Such means are schematically illustrated in FIG. 6A, which illustrates a tissue press 300 having a known torque wrench assembly included therein.

The press 300 includes a base 302. Attached to the base in the manner described above is a first forming part 304. Also attached to the base is a saddle 306. Received in the saddle 306 is the connector portion 308 of a handle assembly 310. The press 300 also includes a pivot pin 312 pivotally interconnecting the handle assembly 310 and the base 302.

The handle assembly 310 includes a form-supporting portion 314 to which there is attached in the manner described above a second forming part 316. The handle assembly 310 also includes a second portion 318 connected to the form-supporting portion 314 by a drive mechanism 320. The second portion 318 includes a knurled section 322 which is rotatable about an axis 324. On the second portion 318 there is a gauge 326.

The knurled section 322 is rotatable about the axis 324 to set the torque value desired and as shown on the gauge 326. Thereafter, the handle assembly 310 can be pivoted toward the base 302 in the direction indicated by the arrow 328 only until the preset amount of torque is applied. At that point, no more torque is transferred through the drive mechanism 320 to the form-supporting portion 314. This limits the amount of pressure applied to the tissue by the second forming part 316, that is, blocks application to the tissue of force in excess of a predetermined amount.

It should be understood that the torque wrench assembly or construction indicated in FIG. 6A is only illustrative of the many ways in which the amount of pressure applied to the tissue by the tissue press can be limited to a predetermined amount. There are other known mechanisms for performing the same function, and their use is included within the scope of the present invention.

Figures 7, 7A:
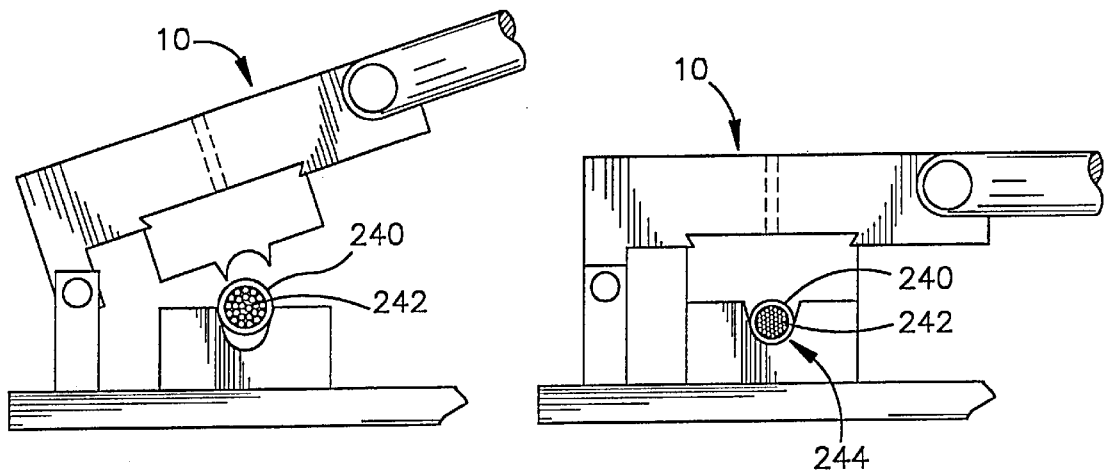
FIGS. 7 and 7A illustrate a composite tissue graft such as compression of bone around tendon.

FIGS. 7 and 7A illustrate the use of a tissue press in accordance with the present invention to form a composite graft. As discussed above, with the present invention, it is also possible to make a composite graft. For example, the graft material for an anterior cruciate ligament (fibrous connective tissue) reconstruction is preferably tendon in the middle with bone at both ends. In accordance with the apparatus and method of the present invention, bone tissue can be compressed around the ends of the tendon tissue to form a substitute anterior cruciate ligament more closely approximating the original.

Thus, as illustrated schematically in FIGS. 7 and 7A, the tissue press 10 of FIGS. 1–4 is being used to compress bone tissue 240 around tendon tissue 242 to form a substitute anterior cruciate ligament 244. The tendon (fibrous connective tissue) 242 can be harvested from one site and the bone 240 can be harvested from another site.

It should be understood that the graft can be multiple tissue fragments rather than a composite material. Thus, the tissue press 10, or indeed any tissue press in accordance with the present invention, can be used to compress, for example, multiple bone fragments into one large piece. It should also be understood that the tissue press in accordance with the present invention can be used to add additional materials to body tissue material by pressure. For example, to bone tissue there can be added a carrier such as gelatin, tri-calcium phosphate, an antibiotic, hydroxyapatite, allografts or autrogratfs, or any other polymeric. Many of the additional materials, for example, the antibiotics and hydroxyapatite, are medicinal substances. This process is believed to be self-explanatory in light of the foregoing description, but for reference may be understood by referring to FIGS. 7 and 7A wherein 240 would be the bone tissue or other tissue to which material is being added (squeezed in under pressure), and 242 indicates the additional material being added to the tissue 240.

In this case, fibrin can be highly suitable for use as such an additional material. Fibrin is a blood component important in blood clotting. It can be separated or centrifuged from blood and has the nature of an adhesive gel. Fibrin can be used as an adhesive, either in a natural state or after being compressed, to hold together material such as separate tissue pieces pressed together in a tissue press of the present invention.

Figure 8:
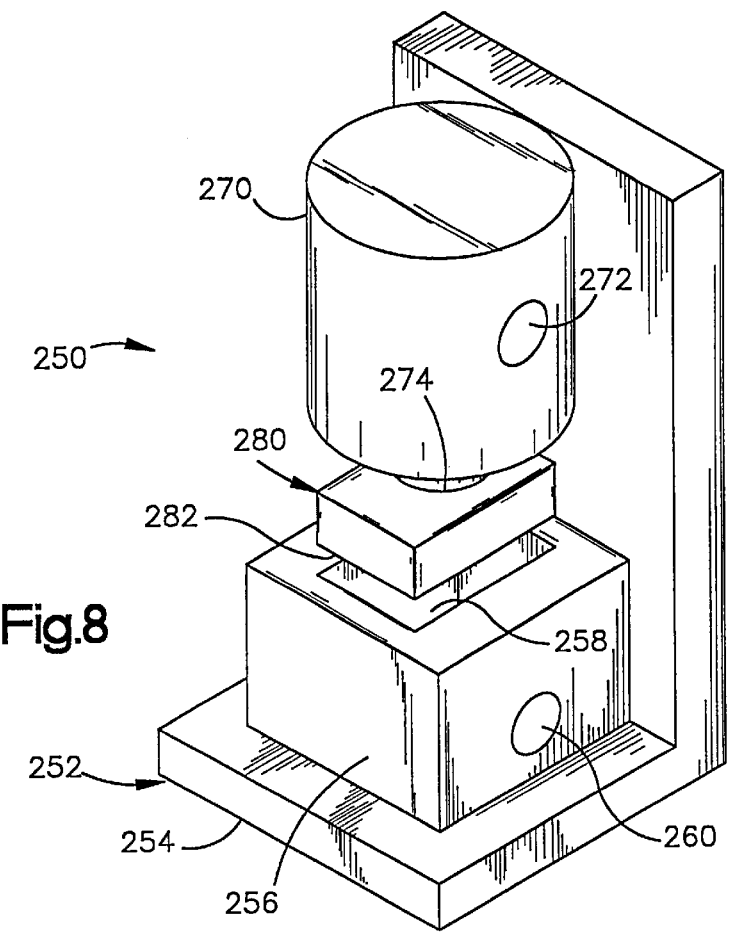
FIG. 8 is a view of a tissue press in accordance with a fourth embodiment of the invention illustrating extrusion of tissue graft material.

In a fourth embodiment of the invention, illustrated in FIG. 8, a tissue press 250 is operated to extrude rather than press material. The press 250 includes a base 252 having a support surface 254 for supporting the base 252 and thus the press 250 on a table or other support (not shown). A die 256 is attached to the base 252. The die 256 may be slidably or otherwise attached to the base 252 in any suitable manner which blocks movement of the die 256 relative to the base 252 during operation of the press 250 and which allows for easy interchange of forming elements 256. The die 256 has an upwardly facing opening 258. An extrusion opening 260 is in fluid communication with the opening 258 of the die 256.

An air or hydraulic cylinder 270 is fixed to the base 252 above the die 156. The cylinder 270 has a port 272 for the introduction of air or other fluid under pressure to operate a piston 274 in a known manner. A ram 280 is connected to the piston 274. The ram 280 has a surface 282 facing the opening 258 on the die 256.

In operation of the press 250, a die 256 is selected which will extrude tissue in the desired shape. The die 256 is attached to the base 252. A piece of tissue to be extruded (not shown) is placed in the opening 258 of the die 256. The cylinder 270 is then actuated to move the ram 280 toward the die 256. The surface 282 on the ram 280 engages the tissue, and forces the tissue into and through the die 256, exiting through the opening 260. The tissue is extruded in the desired shape. As discussed above, a fluid drain port can be provided in the press 250.

It can also be useful to heat or cool the tissue being worked in a tissue press of the present invention. Accordingly, the present invention contemplates the use of means for selectively controlling the temperature of the piece of tissue while it is being compressed or shaped. As an example, illustrated schematically in FIG. 4 is a fluid passage 284 extending from the outer surface of the forming element 124 and around the forming surface 128 thereof. Fluid which is either heated or cooled flows through the passage 284 and either cools or heats the material of the forming element 124 in the area adjacent the forming surface 128. Thus, the tissue, when it comes in contact with the forming surface 128, can be selectively heated or cooled during the compression or reshaping operation. Heating can be useful in holding together materials being compressed, for example, and cooling can be useful to avoid tissue damage arising from overheating of tissue being compressed. It should be understood that other means of achieving these functions are contemplated, such as electrical heating elements. Further, both forming elements can be heated or cooled rather than just one. Any such equivalent structure is to be considered within the scope of the present invention.

In accordance with another feature of the present invention, a retainer is provided for retaining tissue graft material in its compressed state. After the graft is compressed, the retainer is placed around the graft. The retainer can help to maintain the graft in a compressed configuration or in a specific shape for a period of time long enough to be placed in the body.

The retainer may be one of many different shapes. The shape of the retainer is chosen to meet the specific application. There are a number of suitable shapes, such as a ring, a cylinder, a cage, a rectangular shape, a mesh, a suture-like wrap, etc. Some of these are illustrated schematically in FIGS. 9A–9F. It should be understood that this is not an exhaustive listing, but rather that these are merely exemplary of the principle involved, and accordingly, the invention is not limited to these particular shapes. For example, a retainer may be provided which is in the particular shape of the tissue material being compressed, which can be rectangular, cylindrical, planar, etc.

Figures 9A, 9D:
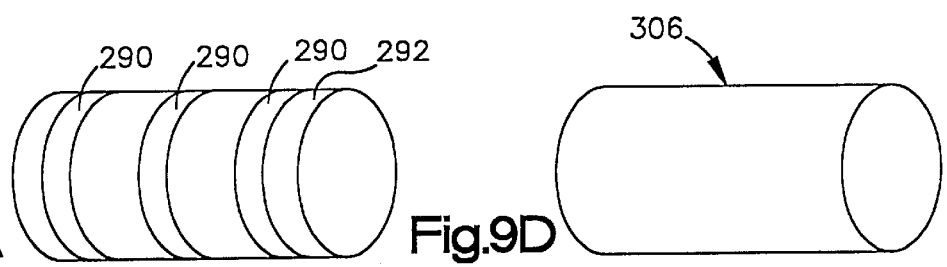
FIGS. 9A–9F illustrates a plurality of different retainers for compressed tissue.
Figures 9B, 9E:
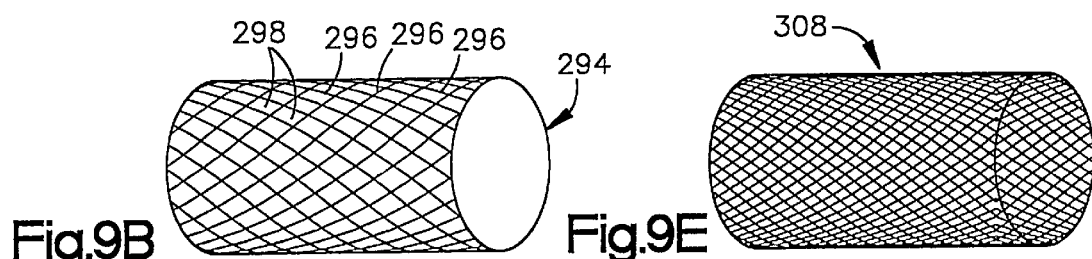
Figures 9C, 9F:
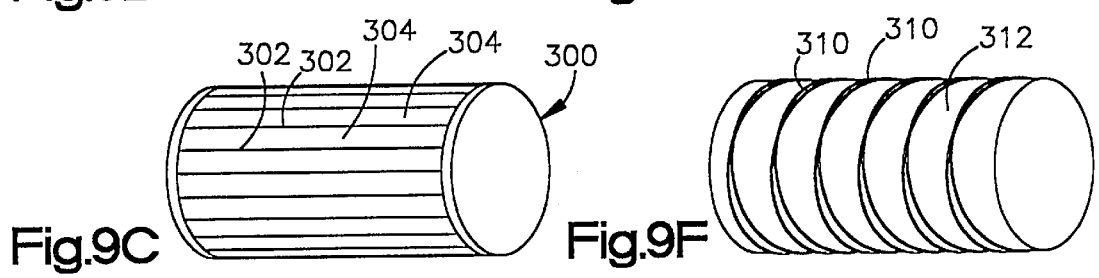

FIG. 9A illustrates a plurality of bands or rings 290 used to hold together compressed tissue 292. FIG. 9B illustrates a cage 294 which can be used to hold together the compressed tissue 292 of FIG. 9A. The cage 294 includes a plurality of crossed filaments 296 which define between them a series of openings 298 for tissue ingrowth. FIG. 9C illustrates another cage 300 which can be used to hold together the compressed tissue 292 of FIG. 9A. The cage 300 includes a plurality of longitudinally extending filaments 302 which define between them a series of openings 304 for tissue ingrowth. FIG. 9D illustrates a solid-walled cylinder 306 which can be used to hold together the compressed tissue 292. FIG. 9E illustrates a mesh cylinder 308 which can be used to hold together the compressed tissue 292. FIG. 9F illustrates the wrapping of a cord or suture 310 around compressed tissue 312.

Any of these retainers may be made of various materials. The material of the retainer is chosen to meet the specific application. Some of the many materials which are suitable are biodegradable materials, ceramics (especially with bone-growth enhancers, hydroxyapatite, etc.); polymeric material such as Dacron or other known surgical plastics; metal; or composite materials.

In use, the graft material may be pushed into the retainer structure after graft material is compressed. Alternatively, the graft material may be compressed with the retainer structure. After the graft material is compressed in the retainer, the combined structure of graft plus retainer is placed in the host site in the body. The retainer helps to maintain the graft in a compressed configuration or in the specific shape into which it was compressed for a period of time long enough to be placed in the body.

If the retainer is made of a biodegradable material, then the retainer degrades and disappears after a period of time. If the retainer is not made of a biodegradable material, then the retainer remains in the body. Tissue ingrowth occurs to bind the host tissue to the graft material. Tissue ingrowth through and around the retainer, between the host tissue and the graft material, is promoted if there are openings as discussed above in the retainer.

The invention, the retainer may, if desired, be made of a material which expands after it is placed in the body, to mechanically interlock the graft to the body. The expansion can take place in one of two ways. First, the retainer can itself be compressed, as with the tissue, then expand when placed in the body. Second, the retainer can be made of a material which expands when it comes in contact with water or other bodily fluids.

(It should be noted that the tissue can itself be compressed then expand when contacted by water. As an example, a tendon can be compressed in a desiccated state, and as it imbibes water it expands and creates a firmer lock or tighter fit in the host site.)

The expandable material can first be compressed with the tissue being grafted, and which then expands when placed in the body. The retainer is preferably made of a material which has more structural stability than the tissue being grafted, and provides mechanical integrity and structural support for the graft tissue. A retainer made of a solid polymeric material, for example, is useful to retain in a compressed state a tendon or bone tissue graft.

These expandable materials can be used not only to retain graft material, but for any shape required for stabilization surgery, such as a wedge, screw, rivet, retaining ring, or spacer, an intramedullary rod, a joint replacement part such as a femoral component of acetabular cup, an expandable sleeve, or another mechanical structure. The expandable materials thus can be used both as a carrier or retainer for another material (e.g. tissue graft material) and on their own as a prosthetic element.

There are a number of suitable materials which expand when they come in contact with water or other fluids. One is PEEKX (polyether-etherketone). A desiccated biodegradable material, or a desiccated allograft may also be used.

As a simple example, an expandable retainer 330 (FIG. 10A) with graft tissue 332 therein is placed into a tissue or bone space 334 defined by an edge 336 in host tissue 338. As the retainer 330 imbibes body fluids or water from the host tissue 338, it expands radially outwardly into the tissue or bone space 334 and creates a mechanical interlock (FIG. 10B). It also expands radially inwardly and clamps on the graft tissue 332. Therefore, the graft tissue 332 is locked into the host site, without the necessity of damaging the tissue further through some other kind of attachment means.

For example, a hip replacement (femoral head) is typically made of metal. To implant the replacement, the softer, inner cancellous bone of the femur is first removed. The inner surface of the cortical bone is then machined to provide a close fit between the external surface of the replacement and the hard outer cortical bone material. All this requires a substantial opening in the femur and still does not guarantee a close enough fit for the implant.

If, instead, the implant is made of an expanding material such as PEEK, only a smaller opening is needed, thus reducing trauma to the bone. Although it is best to lock against the cortical bone, it is possible to implant solely in the cancellous bone, which because of the expansion of the implant provides a better fit than a metal implant. A benefit of implanting in the cancellous bone is reduction of the danger of putting the implant in so tightly that the cortical bone is split (wedged open). Further, if the opening in the bone is not exactly the same shape as the outer surface of the implant, the implant expands to provide a custom contoured fit to the bone and provide immediate mechanical stability. Thus, less machining of the bone is needed, while at the same time obtaining a closer fit.

Thus, as illustrated in FIGS. 11–11B, a hip replacement (femoral head) 340 is made of PEEK or another expandable material. The replacement 340 is inserted into an intramedullary channel 342 cut into a femur 344. The replacement 340 is smaller in diameter than the channel 342. The replacement 340 absorbs body fluids and expands to lock itself into the channel 342 in the femur 344. (It should be understood that the scale shown in FIGS. 11–11B is exaggerated as to the amount by which the replacement 340 expands.)

Similarly, a bone plate or other structure or tissue can be secured to a bone with a fastener made of such an expandable material. As illustrated schematically in FIGS. 12 and 12A, a bone plate 350 is secured to a bone 352. In FIG. 12, a fastener 354 is used which has an unthreaded portion 356 extending into the bone 352. The fastener 354, or at least the unthreaded portion 356, is made of PEEK or another suitable expandable material. The portion 356 imbibes fluid from the bone 352 and expands radially outwardly, from an unexpanded condition as shown in phantom at 358 to an expanded condition as shown in solid lines at 360, to lock the fastener 354 into the bone 352. This enables the securing of the plate 350 to the bone 352 without cutting threads into the bone 352 as is usually done.

In FIG. 12A, a fastener 362 has a threaded portion 364 extending into the bone 352. The threaded portion 364 is made of PEEK or another suitable expandable material. The threaded portion 364 imbibes fluid from the bone 352 and expands radially outwardly to additionally lock the fastener 362 into the bone 352. Alternatively, the fastener 362 of FIG. 12A may have a coating 366 on its portion threaded into the bone 352. The coating 366 is made of PEEK or another suitable expandable material. The coating 366 imbibes fluid from the bone 352 and expands radially outwardly to additionally lock the fastener into the bone 352.

When such a fastener is made of a non-metal expandable material, removal of the fastener simply entails drilling out the center thereof. This is much easier than with a typical metal bone screw.

From the above description of the invention, those skilled in the art will perceive improvements, changes and modifications. Such improvements, changes and modifications within the skill of the art are intended to be covered by the appended claims.

I claim:

1. A method of using body tissue, said method comprising the steps of obtaining graft tissue from at least one bone, removing liquid from the graft tissue, adding a medicinal substance to the graft tissue, shaping the graft tissue to which the medicinal substance has been added to a predetermined configuration while the graft tissue is outside a patient's body, moving the graft tissue to which the medicinal substance has been added into the patients' body while the graft tissue has the predetermined configuration, and allowing expansion of the graft tissue in the patient's body and absorption of liquid from the patient's body into the graft tissue.

2. A method as set forth in claim 1 wherein said step of shaping the graft tissue to which the medicinal substance has been added to a predetermined configuration includes compressing the graft tissue from a first volume to a second volume, said step of moving the graft tissue to which the medicinal substance has been added into the patient's body includes positioning the graft tissue adjacent to a bone in the patient's body with the graft tissue in a compressed condition.

3. A method as set forth in claim 1 further including the step of maintaining the graft tissue in a viable living condition during said step of removing liquid from the graft tissue and said step of shaping the graft tissue.

4. A method as set forth in claim 1 further including the step of establishing a mechanical interlock between the graft tissue and tissue in the patient's body during expansion of the graft tissue and absorption of liquid from the patient's body.

5. A method as set forth in claim 1 wherein said step of obtaining graft tissue includes obtaining a plurality of pieces of graft tissue, said step of shaping the graft tissue to a predetermined configuration includes forming the plurality of pieces of graft tissue into one piece having the predetermined configuration, said step of moving the graft tissue into the patient's body while the graft tissue has the predetermined configuration includes moving the one piece having the predetermined configuration into the patent's body.

6. A method as set forth in claim 5 further including the step of establishing a mechanical interlock between the one piece and tissue in the patient's body during expansion of the graft tissue and absorption of liquid from the patient's body.

7. A method as set forth in claim 1 wherein said step of obtaining graft tissue includes obtaining a plurality of pieces of graft tissue, said method further includes adding fibrin to the plurality of pieces of graft tissue, said step of adding a medicinal substance to the graft tissue includes adding the medicinal substance to the plurality of pieces of graft tissue, said step of shaping the graft tissue to the predetermined configuration includes forming the plurality of pieces of graft tissue to which the fibrin and medicinal substance have been added into one piece having the predetermined configuration, said step of moving the graft tissue into the patient's body while the graft tissue has the predetermined configuration includes moving the one piece having the predetermined configuration into the patient's body.

8. A method as set forth in claim 7 further including the step of establishing a mechanical interlock between the one piece and tissue in the patient's body during expansion of the graft tissue and absorption of liquid from the patient's body.

9. A method as set forth in claim 1 wherein said step of shaping the graft tissue to a predetermined configuration includes heating the graft tissue.

10. A method as set forth in claim 1 wherein said step of shaping the graft tissue to a predetermined configuration includes cooling the graft tissue.

11. A method as set forth in claim 1 wherein said step of adding a medicinal substance to the graft tissue includes adding physiologic solution to the graft tissue.

12. A method as set forth in claim 1 wherein said step of adding a medicinal substance to the graft tissue includes adding bone growth enhancers to the graft tissue.

13. A method as set forth in claim 1 wherein said step of adding a medicinal substance to the graft tissue includes adding polysaccharides to the graft tissue.

14. A method as set forth in claim 1 wherein said step of adding a medicinal substance to the graft tissue includes adding antibiotics to the graft tissue.

15. A method as set forth in claim 1 wherein said step of adding a medicinal substance to the graft tissue includes adding synthetic bone materials to the graft tissue.

16. A method as set forth in claim 1 wherein said step of adding a medicinal substance to the graft tissue includes adding tri-calcium phosphate to the graft tissue.

17. A method as set forth in claim 1 wherein said step of adding a medicinal substance to the graft tissue includes adding hydroxyapatite to the graft tissue.

18. A method of using body tissue, said method comprising the steps of obtaining graft tissue from at least one bone, adding a medicinal substance to the graft tissue, changing the graft tissue from a first volume to a second volume which is less than the first volume after adding the medicinal substance to the graft tissue, positioning at least a portion of the graft tissue and medicinal substance adjacent to a bone in the patient's body after performing said step of changing the volume of the graft tissue, and allowing expansion of the graft tissue in the patient's body and the absorption of liquid from the patient's body into the graft tissue.

19. A method as set forth in claim 18 further including the step of maintaining the graft tissue in a viable living condition during said step of changing the volume of the graft tissue.

20. A method as set forth in claim 18 further including the step of establishing a mechanical interlock between the graft tissue and tissue in the patient's body during expansion of the graft tissue and absorption of liquid from the patient's body.

21. A method as set forth in claim 18 wherein said step of obtaining graft tissue includes obtaining a plurality of pieces of graft tissue, said step of changing the volume of the graft tissue includes forming the plurality of pieces of graft tissue into one piece having the second volume, said step of positioning the graft tissue and medicinal substance adjacent to a bone in the patient's body includes moving the one piece having the second volume into the patient's body.

22. A method as set forth in claim 21 further including the step of establishing a mechanical interlock between the one piece and tissue in the patient's body during expansion of the graft tissue and absorption of liquid from the patient's body.

23. A method as set forth in claim 18 wherein said step of obtaining graft tissue includes obtaining a plurality of pieces of graft tissue, said method further includes adding fibrin to the plurality of pieces of graft tissue, said step of adding a medicinal substance to the graft tissue includes adding the medicinal substance to the plurality of pieces of graft tissue, said step of changing the volume of the graft tissue includes forming the plurality of pieces of graft tissue to which the fibrin and medicinal substance have been added into one piece having the predetermined configuration, said step of positioning the graft tissue in the patient's body includes moving the one piece having the predetermined configuration into the patient's body.

24. A method as set forth in claim 23 further including the step of establishing a mechanical interlock between the one piece and tissue in the patient's body during expansion of the graft tissue and absorption of liquid from the patient's body.

25. A method as set forth in claim 18 wherein said step of changing the volume of the graft tissue to the second volume includes heating the graft tissue.

26. A method as set forth in claim 18 wherein said step of changing the volume of the graft tissue to the second volume includes cooling the graft tissue.

27. A method as set forth in claim 18 wherein said step of adding a medicinal substance to the graft tissue includes adding physiologic solution to the graft tissue.

28. A method as set forth in claim 18 wherein said step of adding a medicinal substance to the graft tissue includes adding bone growth enhancers to the graft tissue.

29. A method as set forth in claim 18 wherein said step of adding a medicinal substance to the graft tissue includes adding polysaccharides to the graft tissue.

30. A method as set forth in claim 18 wherein said step of adding a medicinal substance to the graft tissue includes adding antibiotics to the graft tissue.

31. A method as set forth in claim 18 wherein said step of adding a medicinal substance to the graft tissue includes adding synthetic bone materials to the graft tissue.

32. A method as set forth in claim 18 wherein said step of adding a medicinal substance to the graft tissue includes adding tri-calcium phosphate to the graft tissue.

33. A method as set forth in claim 18 wherein said step of adding a medicinal substance to the graft tissue includes adding hydroxyapatite to the graft tissue.

34. A method of using body tissue, said method comprising the steps of obtaining graft tissue, adding a medicinal substance to the graft tissue, shaping the graft tissue to a predetermined configuration, moving the graft tissue to which the medicinal substance has been added into the patient's body while the graft tissue has the predetermined configuration, allowing expansion of the graft tissue in the patient's body and absorption of liquid from the patient's body into the graft tissue, and establishing a mechanical interlock between the graft tissue and tissue in the patient's body during expansion of the graft tissue and absorption of liquid from the patient's body.

35. A method as set forth in claim 34 wherein said step of shaping the graft tissue to a predetermined configuration is performed after adding the medicinal substance to the graft tissue and includes changing the volume of the graft tissue from a first volume to a second volume, said step of moving the graft tissue to which the medicinal substance has been added into the patient's body includes positioning the graft tissue adjacent to a bone in the patient's body.

36. A method as set forth in claim 34 further including the step of maintaining the graft tissue in a viable living condition during said step of shaping the graft tissue.

37. A method as set forth in claim 34 wherein said step of obtaining graft tissue includes obtaining a plurality of pieces of graft tissue, said step of shaping the graft tissue to a predetermined configuration includes forming the plurality of pieces of graft tissue into one piece having the predetermined configuration, said step of moving the graft tissue into the patient's body while the graft tissue has the predetermined configuration includes moving the one piece having the predetermined configuration into the patient's body.

38. A method as set forth in claim 34 wherein said step of obtaining graft tissue includes obtaining a plurality of pieces of graft tissue, said method further includes adding fibrin to the plurality of pieces of graft tissue, said step of adding a medicinal substance to the graft tissue includes adding the medicinal substance to the plurality of pieces of graft tissue, said step of shaping the graft tissue to the predetermined configuration includes forming the plurality of pieces of graft tissue to which the fibrin and medicinal substance have been added into one piece having the predetermined configuration, said step of moving the graft tissue into the patient's body while the graft tissue has the predetermined configuration includes moving the one piece having the predetermined configuration into the patient's body.

39. A method as set forth in claim 34 wherein said step of shaping the graft tissue to predetermined configuration includes heating the graft tissue.

40. A method as set forth in claim 34 wherein said step of shaping the graft tissue to a predetermined configuration includes cooling the graft tissue.

41. A method as set forth in claim 34 wherein said step of adding a medicinal substance to the graft tissue includes adding physiologic solution to the graft tissue.

42. A method as set forth in claim 34 wherein said step of adding a medicinal substance to the graft tissue includes adding bone growth enhancers to the graft tissue.

43. A method as set forth in claim 34 wherein said step of adding a medicinal substance to the graft tissue includes adding polysaccharides to the graft tissue.

44. A method as set forth in claim 34 wherein said step of adding a medicinal substance to the graft tissue includes adding antibiotics to the graft tissue.

45. A method as set forth in claim 34 wherein said step of adding a medicinal substance to the graft tissue includes adding synthetic bone materials to the graft tissue.

46. A method as set forth in claim 34 wherein said step of adding a medicinal substance to the graft tissue includes adding tri-calcium phosphate to the graft tissue.

47. A method as set forth in claim 34 wherein said step of adding a medicinal substance to the graft tissue includes adding hydroxyapatite to the graft tissue.

48. A method of using body tissue, said method comprising the steps of obtaining a plurality of pieces of graft tissue, adding a medicinal substance to the plurality of pieces of graft tissue, forming the plurality of pieces of graft tissue to which the medicinal substance has been added into one piece having a desired configuration while the graft tissue is outside a patient's body, moving the one piece having the desired configuration into the patient's body, and allowing expansion of graft tissue in the one piece in the patient's body and absorption of liquid from the patient's body into the graft tissue in the one piece.

49. A method as set forth in claim 48 further including the step of cutting off excess graft tissue from the one piece contemporaneously with performing said step of forming the plurality of pieces of graft tissue to which the medicinal substance has been added into one piece having a desired configuration.

50. A method as set forth in claim 48 wherein said step of obtaining a plurality of pieces of graft tissue includes obtaining at least one piece of bone and at least one piece of fibrous connective tissue, said step of forming the plurality of pieces of graft tissue into one piece having a desired configuration includes interconnecting the one piece of bone and the one piece of fibrous connective tissue.

51. A method as set forth in claim 48 wherein said step of obtaining a plurality of pieces of graft tissue includes obtaining a plurality of pieces of bone, said step of forming the plurality of pieces of graft tissue into one piece having a desired configuration includes interconnecting the plurality of pieces of bone.

52. A method as set forth in claim 51 further including the step of adding fibrin to the plurality of pieces of graft tissue, said step of forming the plurality of pieces of graft tissue into one piece is performed after adding fibrin to the plurality of pieces of graft tissue.

53. A method as set forth in claim 48 further including the step of removing liquid from the plurality of pieces of graft tissue.

54. A method as set forth in claim 48 wherein said step of forming the plurality of pieces of graft tissue into one piece having a desired configuration includes compressing the graft tissue from a first volume to a second volume, said step of moving the one piece having the desired configuration into the patient's body includes positioning the graft tissue adjacent to a bone in the patient's body with the graft tissue in a compressed condition.

55. A method as set forth in claim 48 further including the step of maintaining the graft tissue in a viable living condition during said step of forming the plurality of pieces of graft tissue into one pieces.

56. A method as set forth in claim 48 further including the step of establishing a mechanical interlock between the graft tissue and tissue in the patient's body during expansion of the graft tissue and absorption of liquid from the patient's body.

57. A method as set forth in claim 48 wherein said step of shaping the graft tissue to a desired configuration includes heating the graft tissue.

58. A method as set forth in claim 48 wherein said step of shaping the graft tissue to a desired configuration includes cooling the graft tissue.

59. A method of using body tissue, said method comprising the steps of obtaining a plurality of pieces of bone, adding a medicinal substance to the plurality of pieces of bone, forming the plurality of pieces of bone into one piece having a desired configuration while the plurality of pieces of bone are outside a patient's body, said step of forming the plurality of pieces of bone into one piece includes reducing the volume of a space occupied by the plurality of pieces of bone from a first volume to a second volume which is less than the first volume, moving the one piece having the desired configuration into the patient's body while the plurality of pieces of bone in the one piece occupy a space having a volume which is less than the first volume, and allowing expansion of the plurality of pieces of bone in the one piece and absorption of liquid from the patient's body by the plurality of pieces of bone in the one piece.

60. A method as set forth in claim 59 further including the step of establishing an interlock between the plurality of pieces of bone in the one piece and tissue in the patient's body during expansion of the plurality of pieces of bone.

61. A method of using body tissue, said method comprising the steps of obtaining a plurality of pieces of graft tissue including at least one piece of bone and at least one piece of fibrous connective tissue, interconnecting at least the one piece of bone and at least the one piece of fibrous connective tissue to form a graft assembly, moving the graft assembly into the patient's body, and allowing expansion of the graft assembly in the patient's body and absorption of liquid from the patient's body.

62. A method as set forth in claim 61 further including the step of establishing a mechanical interlock between the graft assembly and tissue in the patient's body during expansion of the graft assembly.

63. A method as set forth in claim 61 further including the step of adding a medicinal substance to the plurality of pieces of graft tissue.

64. A method as set forth in claim 61 further including the step of removing liquid from at least some of the pieces of graft tissue of the plurality of pieces of graft tissue.

65. A method as set forth in claim 61 wherein said step of interconnecting at least the one piece of bone and at least one piece of fibrous tissue includes compressing at least some of the pieces of graft tissue of the plurality of pieces of graft tissue from a first volume to a second volume which is less than the first volume.

66. A method of using body tissue, said method comprising the steps of obtaining graft tissue, shaping the graft tissue to a predetermined configuration, said step of shaping the graft tissue to a predetermined configuration includes heating the graft tissue, moving the graft tissue into the patient's body while the graft tissue has the predetermined configuration, and allowing expansion of the graft tissue in the patient's body and absorption of liquid from the patient's body into the graft tissue.

67. A method as set forth in claim 66 wherein said step of shaping the graft tissue to a predetermined configuration includes changing the volume of the graft tissue from a first volume to a second volume, said step of moving the graft tissue into the patient's body includes positioning the graft tissue adjacent to a bone in the patient's body while the graft tissue has the second volume.

68. A method as set forth in claim 66 further including the step of maintaining the graft tissue in a viable living condition during said step of shaping the graft tissue.

69. A method as set forth in claim 66 wherein said step of obtaining graft tissue includes obtaining a plurality of pieces of graft tissue, said step of shaping the graft tissue to a predetermined configuration includes forming the plurality of pieces of graft tissue into one piece having the predetermined configuration, said step of moving the graft tissue into the patient's body while the graft tissue has the predetermined configuration includes moving the one piece having the predetermined configuration into the patient's body.

70. A method as set forth in claim 66 wherein said step of obtaining graft tissue includes obtaining a plurality of pieces of graft tissue, said method further includes adding fibrin to the plurality of pieces of graft tissue, said step of shaping the graft tissue to the predetermined configuration includes forming the plurality of pieces of graft tissue to which the fibrin substance have been added into one piece having the predetermined configuration, said step of moving the graft tissue into the patient's body while the graft tissue has the predetermined configuration includes moving the one piece having the predetermined configuration into the patient's body.

71. A method of using body tissue, said method comprising the steps of obtaining a plurality of pieces of graft tissue, removing liquid from the plurality of pieces of graft tissue, adding a carrier to the plurality of pieces of graft tissue, forming the plurality of pieces of graft tissue and the carrier into one piece while the graft tissue is outside a patient's body, shaping the plurality of pieces of graft tissue and the carrier to a desired configuration outside of the patient's body, moving the one piece having the desired configuration into the patient's body, and allowing expansion of graft tissue in the one piece in the patient's body and absorption of liquid from the patient's body into the graft tissue in the one piece.

72. A method as set forth in claim 71 further including the step of cutting off excess graft tissue from the one piece contemporaneously with performing said step of forming the plurality of pieces of graft tissue into one piece.

73. A method as set forth in claim 71 further including the step of heating the graft tissue during performance of said step of shaping the plurality of pieces of graft tissue and the carrier to the desired configuration outside of the patient's body.

74. A method as set forth in claim 71 wherein said step of obtaining a plurality of pieces of graft tissue includes obtaining a plurality of pieces of bone, said step of forming the plurality of pieces of graft tissue and the carrier into one piece includes interconnecting the plurality of pieces of bone.

75. A method as set forth in claim 71 further including the step of adding fibrin to the plurality of pieces of graft tissue, said step of forming the plurality of pieces of graft tissue and the carrier into one piece is performed after adding fibrin to the plurality of pieces of graft tissue.

76. A method as set forth in claim 71 wherein said step of forming the plurality of pieces of graft tissue and the carrier into one piece having a desired configuration includes compressing the graft tissue from a first volume to a second volume, said step of moving the one piece having the desired configuration into the patient's body includes positioning the graft tissue adjacent to a bone in the patient's body with the graft tissue in a compressed condition.

77. A method as set forth in claim 71 further including the step of maintaining the graft tissue in a viable living condition during said step of forming the plurality of pieces of graft tissue and the carrier into one piece.

78. A method as set forth in claim 71 further including the step of establishing a mechanical interlock between the graft tissue and tissue in the patient's body during expansion of the graft tissue and absorption of liquid from the patient's body.

79. A method as set forth in claim 71 wherein at least one of said steps of forming the plurality of pieces of graft tissue and the carrier into one piece and shaping the graft tissue to a desired configuration includes heating the graft tissue.

* * * * *